(12) United States Patent
Watanabe

(10) Patent No.: US 7,959,339 B2
(45) Date of Patent: Jun. 14, 2011

(54) ILLUMINATION APPARATUS AND ENDOSCOPE

(75) Inventor: Katsushi Watanabe, Hachioji (JP)

(73) Assignee: Olympus Medical Systems Corp. (JP)

( * ) Notice: Subject to any disclaimer, the term of this patent is extended or adjusted under 35 U.S.C. 154(b) by 124 days.

(21) Appl. No.: 12/210,272

(22) Filed: Sep. 15, 2008

(65) Prior Publication Data

US 2009/0080214 A1 Mar. 26, 2009

(30) Foreign Application Priority Data

Sep. 21, 2007 (JP) ................................ 2007-245483

(51) Int. Cl.
*A61B 1/06* (2006.01)

(52) U.S. Cl. ........ 362/574; 362/580; 362/555; 600/178; 600/101

(58) Field of Classification Search .................. 362/574, 362/580, 555, 294, 554; 600/178, 101
See application file for complete search history.

(56) References Cited

U.S. PATENT DOCUMENTS

| | | | | |
|---|---|---|---|---|
| 1,642,187 A * | 9/1927 | Young, Jr. | ...................... | 600/248 |
| 5,289,555 A | 2/1994 | Sanso | .............................. | 385/92 |
| 5,634,711 A * | 6/1997 | Kennedy et al. | .............. | 362/119 |
| 5,982,969 A * | 11/1999 | Sugiyama et al. | ............. | 385/123 |
| 6,402,347 B1 * | 6/2002 | Maas et al. | ..................... | 362/294 |
| 6,832,849 B2 * | 12/2004 | Yoneda et al. | ................. | 362/551 |
| 6,932,599 B1 * | 8/2005 | Hartung | ........................... | 433/29 |
| 6,976,777 B1 * | 12/2005 | Herold | ............................ | 362/555 |
| 7,198,397 B2 * | 4/2007 | Bennett et al. | ................. | 362/574 |
| 2003/0219207 A1 | 11/2003 | Guy | ................................. | 385/49 |
| 2005/0052883 A1* | 3/2005 | Qi et al. | ......................... | 362/555 |
| 2005/0276553 A1 | 12/2005 | Kazakevich | ................... | 385/115 |
| 2006/0085969 A1 | 4/2006 | Bennett et al. | .................. | 29/600 |
| 2007/0182299 A1* | 8/2007 | Ouderkirk et al. | ............. | 313/110 |
| 2008/0013316 A1* | 1/2008 | Chiang | .......................... | 362/264 |

FOREIGN PATENT DOCUMENTS

JP 5-146403 6/1993

OTHER PUBLICATIONS

International Search Report for corresponding European Patent Application No. 08016454.4-1526 dated Jan. 30, 2009.

* cited by examiner

*Primary Examiner* — Evan Dzierzynski
(74) *Attorney, Agent, or Firm* — Ostrolenk Faber LLP

(57) ABSTRACT

An illumination apparatus includes a light source which generates heat when emitting an illumination light from a light-emitting surface, a light guide bundle which has a light-receiving surface opposed to the light-emitting surface of the light source, to receive the illumination light emitted from the light-emitting surface of the light source, and guides the illumination light from the light source received by the light-receiving surface, and a light guide connector which has an end face arranged along the light guide bundle and opposed to the light-emitting surface of the light source, and a contact part in which at least a part of the end face directly contacts the light-emitting surface, and absorbs the heat generated on the light-emitting surface of the light source.

17 Claims, 10 Drawing Sheets

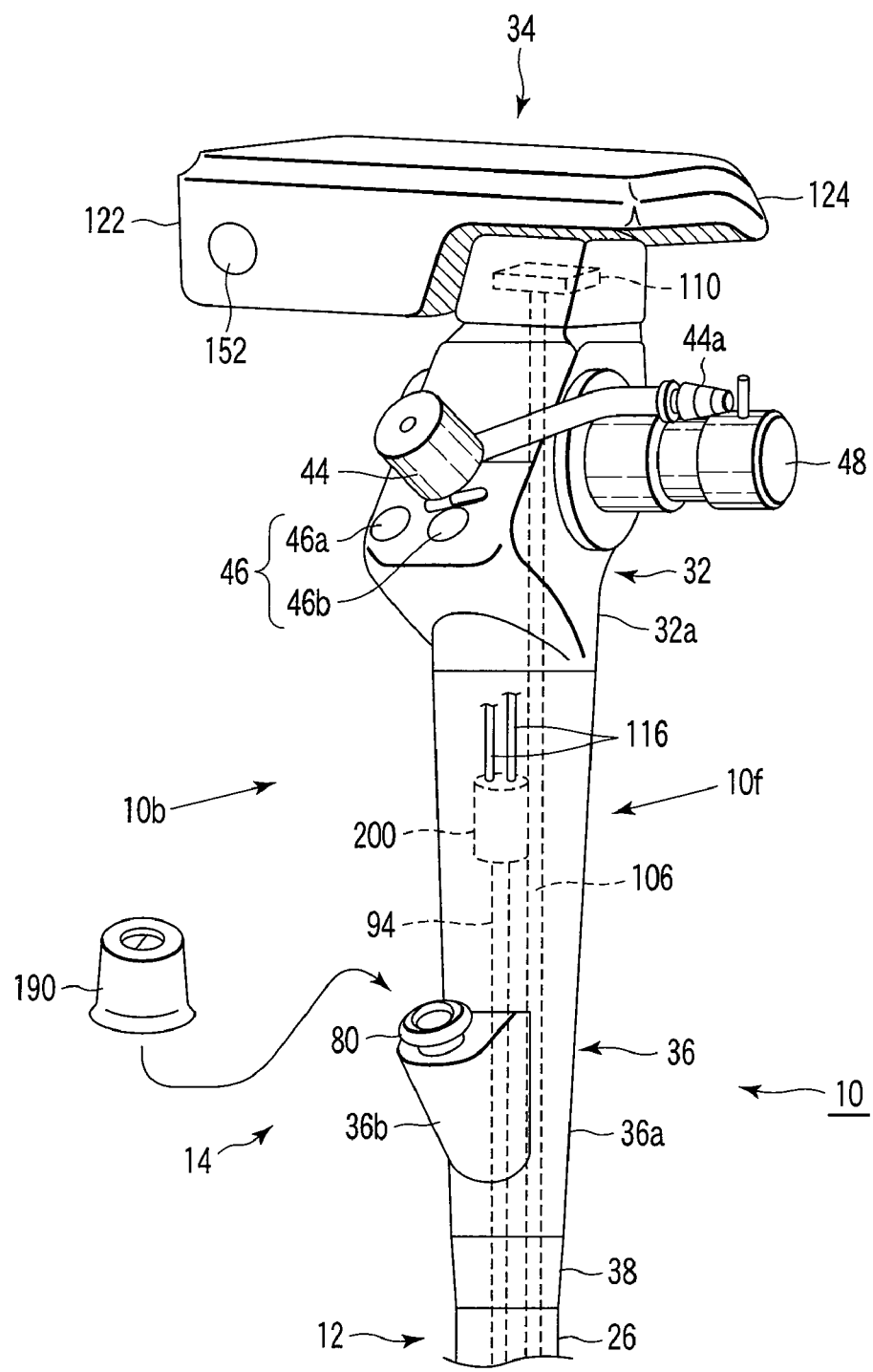
F I G. 3

ILLUMINATION APPARATUS AND ENDOSCOPE

CROSS-REFERENCE TO RELATED APPLICATIONS

This application is based upon and claims the benefit of priority from prior Japanese Patent Application No. 2007-245483, filed Sep. 21, 2007, the entire contents of which are incorporated herein by reference.

BACKGROUND OF THE INVENTION

1. Field of the Invention

The present invention relates to an illumination apparatus requiring radiation of heat from a light source when a light source is provided in a narrow space, for example, and an endoscope having such an illumination apparatus.

2. Description of the Related Art

An LED is provided as a light source of illumination light of an illumination apparatus, which emits light from a distal end of an insertion portion of an endoscope, in a narrow space in an operation portion of the endoscope, as shown in Jpn. Pat. Appln. KOKAI Publication No. H5-146403, for example.

BRIEF SUMMARY OF THE INVENTION

According to an aspect of the invention, there is provided an illumination apparatus including a light source which generates heat when emitting illumination light from a light-emitting surface;

a light transmission member which has a light-receiving surface opposing the light-emitting surface of the light source, to receive the illumination light emitted from the light-emitting surface of the light source, and guides the illumination light from the light source received on the light-receiving surface; and a heat radiation member which has an end face arranged along the light transmission member and opposed to the light-emitting surface of the light source, and a contact part in which at least a part of the end face directly contacts the light-emitting surface, and transmits the light generated in the light source.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a schematic perspective view showing an operation portion of the endoscope, according to first to fourth embodiments;

DETAILED DESCRIPTION OF THE INVENTION

Hereinafter, embodiments of the present invention will be explained with reference to the accompanying drawings. The endoscope explained in the following embodiments is a medical endoscope with excellent transportability, with an image display device built into an operation portion as one piece, and one that is applicable to other industrial fields, as well as the medical field.

Embodiment 1

First, a first embodiment will be explained by using FIG. 1A to FIG. 7D.

Figure 1A:
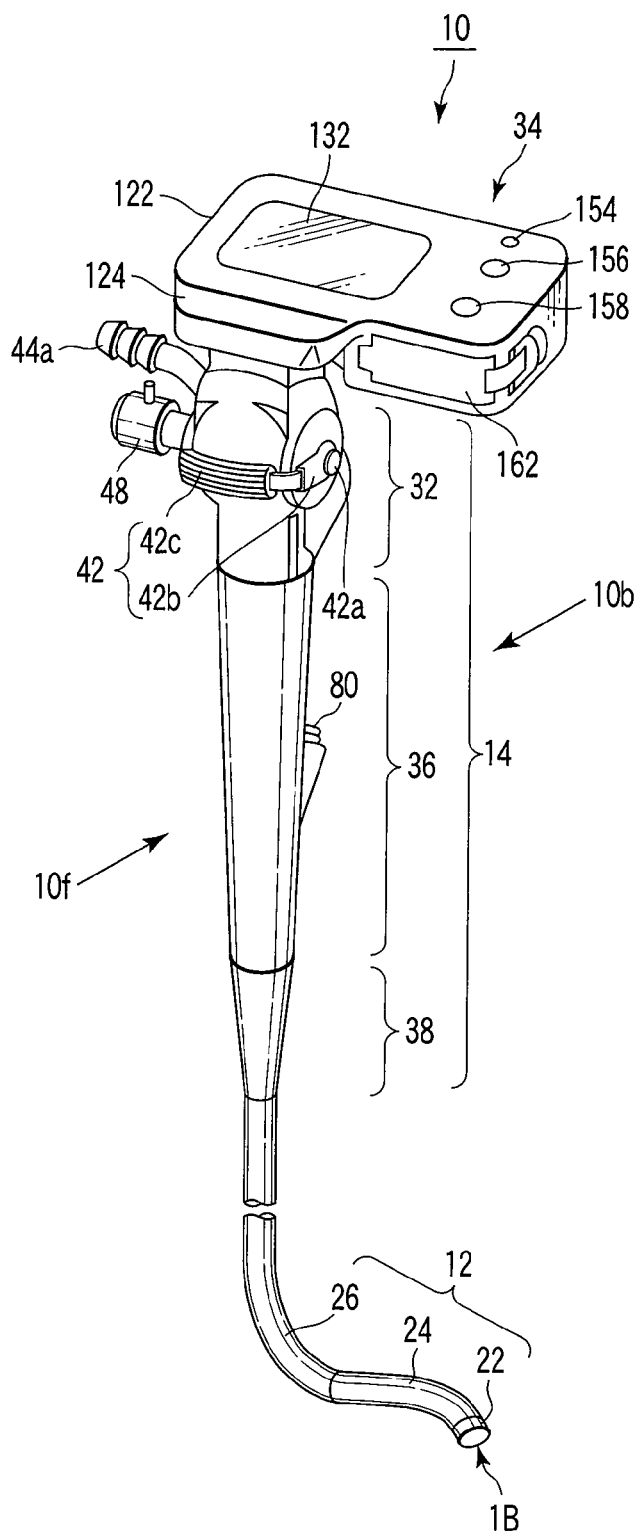
FIG. 1A is a schematic perspective view showing an endoscope according to first to fourth embodiments.
Figure 2:
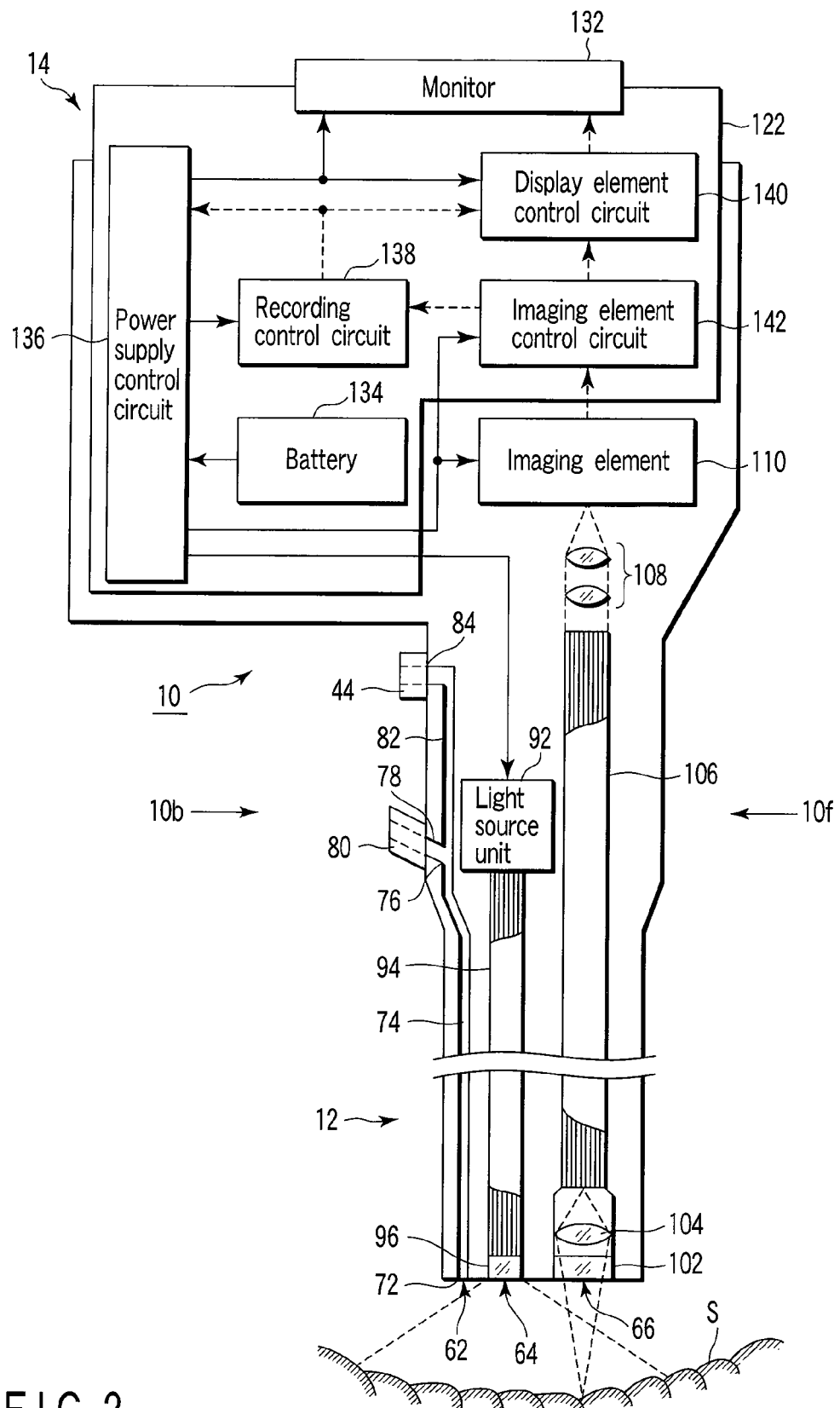
FIG. 2 is a schematic view showing the internal structure of the endoscope according to first to fourth embodiments.

As shown in FIG. 1A and FIG. 2, an endoscope 10 mainly includes an insertion portion 12 to be inserted into an observing area as an observation object in the abdominal cavity, and an operation portion 14 connected to the proximal end of the insertion portion 12.

As shown in FIG. 1A, the insertion portion 12 mainly includes a hard distal end portion 22 provided at the distal end of the insertion portion 12, a bending portion 24 connected to the proximal end of the hard distal end portion 22, and a flexible portion 26 having flexibility formed thin and long and connected to the proximal end of the bending portion 24. The proximal end of the flexible portion 26 is connected to the operation portion 14.

A base material of the hard distal end portion 22 is metal, for example, and the outside surface of the base material is covered with an insulation coating. The bending pieces of the bending portion 24 and a cylindrical braid covering the outside surface of the bending pieces are made of a metallic material, for example. The outside surfaces of the bending pieces and braid are covered with a thin insulation rubber. A helicoidal pipe of the flexible portion 26 is made of a metallic material, for example, and the outside surface of the helicoidal pipe is covered with an insulation tube. The base material of the hard distal end portion 22 is connected to the foremost bending piece of the bending portion 24. The helicoidal pipe is connected to a bending piece closest to the proximal end of the bending pieces in the bending portion 24. An insulation tube made of PTFE is used for a channel tube 74 of a channel 62, described later, to insert the hard distal end portion 22 of the insertion portion 12, the bending pieces and braid of the bending portion 24, and the helicoidal pipe of the flexible portion 26.

As shown in FIG. 1A and FIGS. 3 to 5A, the operation portion 14 mainly includes an operation portion main body 32, an image display device 34 provided at the upper end of the operation portion main body 32, a grip part 36 connected to the lower end of the operation portion main body 32, and a protection hood 38 connected to the lower end of the grip part 36 to prevent buckling of the flexible portion 26.

The grip part 36 is provided between the operation portion main body 32 and insertion portion 12, and grasped by an operator when operating the endoscope 10. The grip part 36 is shaped to be grasped by a thumb T and other fingers of one hand of an operator, for example.

The operation portion main body 32 is provided with a bending control lever 42, a suction button 44 having a suction connector 44a, an image switch 46, and a vent connector 48. The bending control lever 42 is provided on the side of the operation portion main body 32 indicated by the arrow 10f in FIG. 1A (hereinafter called the front side). The suction button 44 and image switch 46 are provided on the side of the operation portion main body 32 indicated by the arrow 10b in FIG. 1A (hereinafter called the rear side). The vent connector 48 is provided on one side of the front side 10f and rear side 10b.

Figure 4:
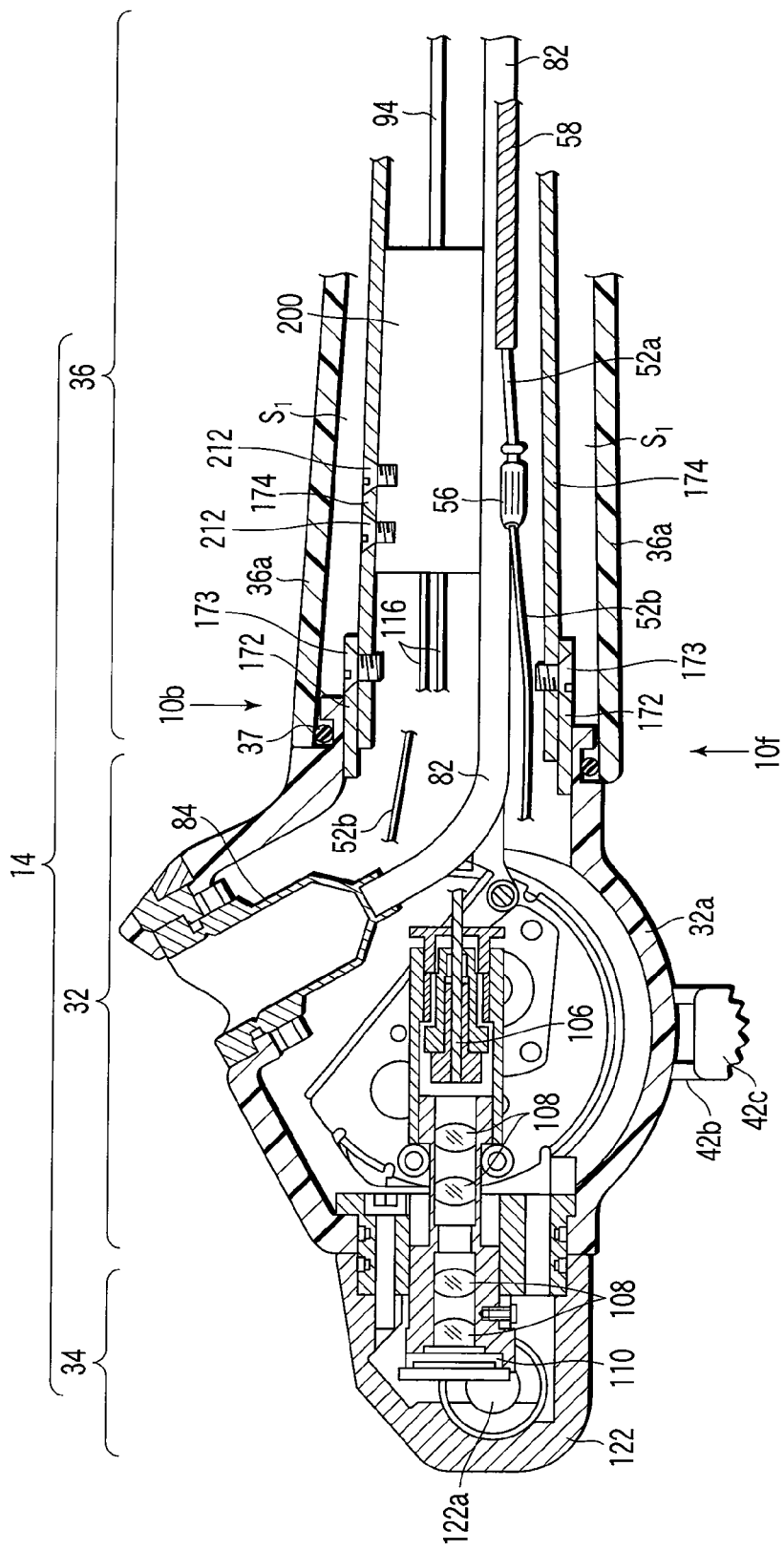
FIG. 4 is a schematic longitudinal sectional view showing an operation portion main body and a grip part of the operation portion of the endoscope, according to first to fourth embodiments.

As shown in FIG. 1A and FIG. 4, the bending control lever 42 includes a pivot 42a, an arm 42b, and a finger rest 42c. The pivot 42a penetrates the operation portion main body 32 in the horizontal direction in FIG. 1A. The pivot 42a is provided on the other side of the front side 10f and rear side 10b (the opposite side of the vent connector 48). The pivot 42a is fixed to a pulley (not shown), on which an operation wire 52 is wound in the operation portion main body 32. One end of the arm 42b is fixed to the pivot 42a. The other end of the arm 42b is connected to the finger rest 42c. The finger rest 42c is provided on the front side 10f closely to the grip part 36, so as to be controlled by the thumb T of the left hand of an operator when grasping the grip part 36. Namely, the arm 42b and finger rest 42c of the bending control lever 42 are substantially L-shaped.

As shown in FIG. 4, a pair of operation wires 52 is connected in the grip part 36 of the operation portion 14 by a wire length adjuster 56. Namely, the operation wires 52 include a first wire 52a and a second wire 52b, respectively.

The distal end of the first wire 52a is fixed to a foremost bending piece of the not-shown bending pieces inside the bending portion 24, or the hard distal end portion 22. The proximal end of the first wire 52a is extended to the inside of the grip part 36 of the operation portion 14 through the flexible portion 26 of the insertion portion 12.

One end of the second wire 52b is fixed to a pulley in the operation portion main body 32, and the other end is extended to the inside of the grip part 36. The first and second wires 52a and 52b are connected by the wire length adjuster 56, so that the wires can be disconnected and the length of each wire can be adjusted. Further, the first wire 52a is covered with a coil-shaped angle coil 58, in substantially the whole length of the protection hood 38 and flexible portion 26, except the bending portion 24 and the part close to the wire length adjuster 56. This prevents friction between the first wire 52a and a connection member 200, to be described later, and breakage of the first wire 52a when contacting other members, thereby protecting the first wire 52a.

Therefore, by operating the bending control lever 42 by hanging a thumb on the finger rest 42c, the operation wire 52 wound around the pulley is moved in the axial direction, and the bending portion 24 is bent.

A suction unit (not shown) is connectable to the suction connector 44a shown in FIG. 1A through a tube (not shown). By operating the suction unit and suction button 44, an operator can suction bodily fluids and phlegm from the abdominal cavity through a channel 62 as a tubular member. As shown in FIG. 2, the channel 62 is extended into the operation portion 14 and insertion portion 12, so that one end (proximal end) is opened to the operation portion main body 32, and the other end (distal end) is opened to the distal end face of the hard distal end portion 22.

The image switch 46 provided on the rear side 10b of the operation portion main body 32 includes an image recording switch 46a and an image reproducing switch 46b. The image recording switch 46a is turned on when recording an image displayed on a monitor 132, described later, of the image display device 34, on a recording medium connected to a recording control circuit 138 (refer to FIG. 2), described later. The image reproducing switch 46b is turned on when an image recorded on a recording medium is reproduced.

On the left side of the operation portion main body 32 in FIG. 1A, the vent connector 48 is provided for supplying air into the insertion portion 12 and operation portion 14 provided with the image display device 34 when checking the endoscope 10 for water leakage. A not-shown cap is detachably fitted to the vent connector 48 to open the inside of the endoscope 10 to the atmosphere to prevent a breakage of the thin rubber covering the outside of the bending portion 24 under negative pressure, when the endoscope 10 is left in negative pressure for sterilization or aerial transportation, for example.

As shown in FIG. 2, a channel 62, illumination optical system 64 and observation optical system 66 are provided in the insertion portion 12 and operation portion 14 of the endoscope 10.

The channel 62 includes an opening 72 (refer to FIG. 1B) of the hard distal end portion 22 of the insertion portion 12, a channel tube 74 (refer to FIG. 5A) connected to the opening 72 to insert the insertion portion 12, a branch part 76 (refer to FIG. 5A) as a heat transmission frame (a heat transmission path), a connection tube 78 (refer to FIG. 5A) as a heat transmission frame, a treatment device insertion port (opening) 80 (refer to FIG. 5A) as an external heat radiation part of the endoscope 10, a suction path 82 (refer to FIG. 4 and FIG. 5A), and a suction button housing 84 (refer to FIG. 4).

Figures 5A, 5B:
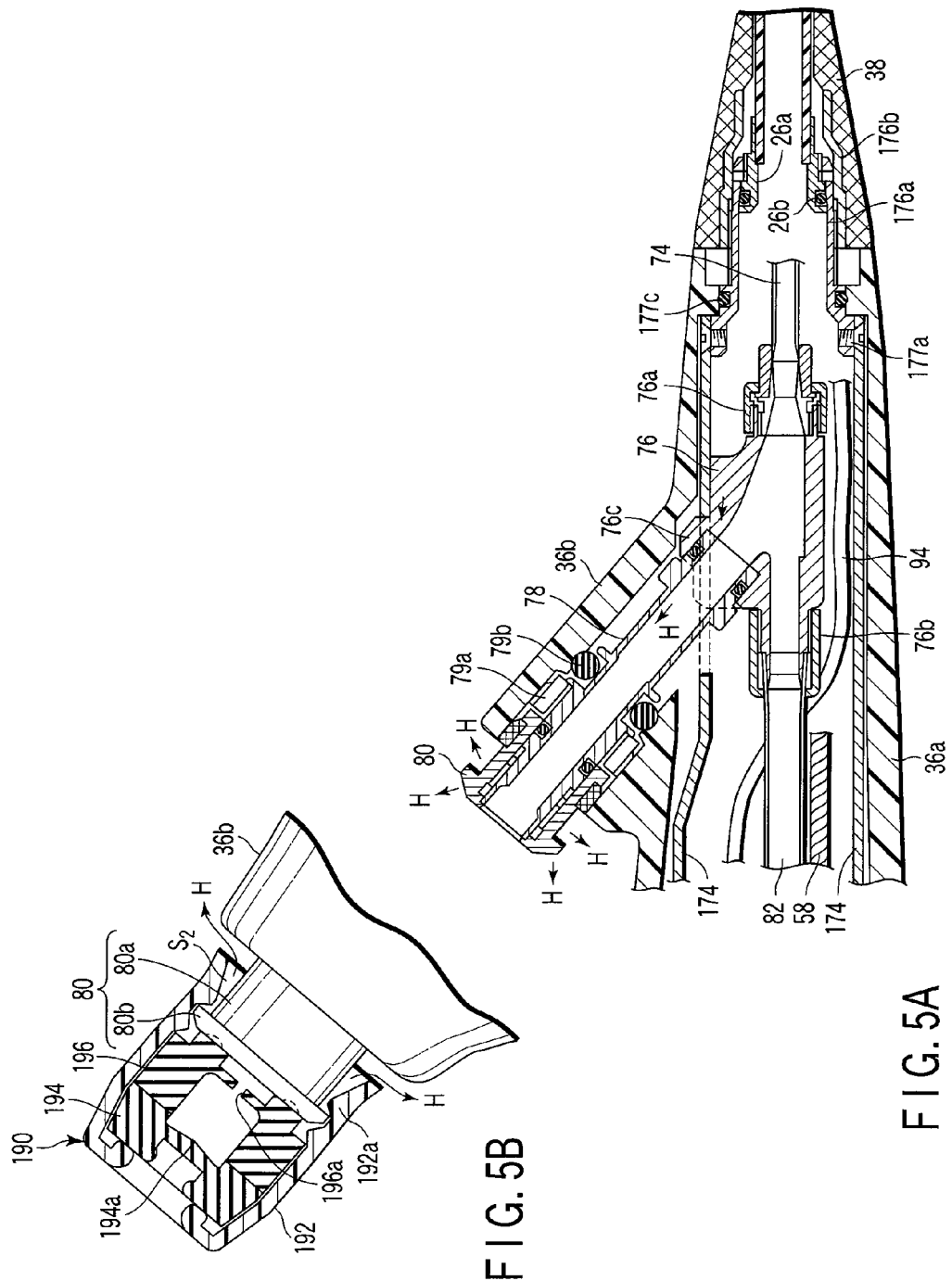
FIG. 5A is a schematic longitudinal sectional view of the grip part and a protection hood of the operation portion of the endoscope, according to first to fourth embodiments.
FIG. 5B is a schematic partial cross sectional view showing the state in which a forceps plug is fitted to a treatment device insertion port provided in the grip part shown in FIG. 5A.

As shown in FIG. 5A, the branch part 76, connection tube 78 and treatment device insertion port 80 are connected. The branch part 76 is connected to a second frame 174, described later, of the grip part 36. Therefore, heat generated in the grip part 36 of the operation portion 14 can be radiated from the second frame 174 to the treatment device insertion port 80 through the connection tube 78.

The suction button 44 having the suction connector 44a is provided in the suction button housing 84. The suction connector 44a and treatment device insertion port 80 are connected inside the operation portion 14. Namely, the suction path 82 and branch part 76 connect the suction button housing 84 to the suction connector 44a, and connect the connection tube 78 to the treatment device insertion port 80.

The suction connector 44a of the operation portion main body 32 is provided on the rear side 10b of the endoscope 10. The suction connector 44a is used to suction bodily fluids and phlegm, for example, from the abdominal cavity. The treatment device insertion port 80 of the grip part 36 is provided on the rear side 10b of the endoscope 10. The treatment device insertion port 80 is used to insert/remove a treatment device into/from the abdominal cavity, by inserting/removing a treatment device such as forceps or the like into/from the channel 62 (refer to FIG. 2).

Figure 1B:
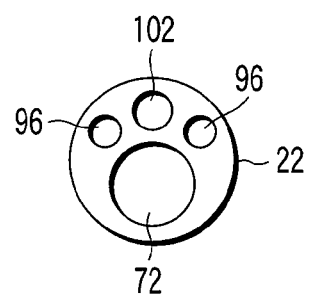
FIG. 1B is a schematic view showing the distal end face of a hard distal end portion indicated by an arrow 1B in FIG. 1A.

As shown in FIG. 2, the illumination optical system (illumination apparatus) 64 includes a light source unit 92, a light guide bundle 94, and an illumination window 96 (refer to FIG. 1B). The observation optical system 66 includes an observation window 102 (refer to FIG. 1B), an objective lens 104, an image guide 106, an image-formation lens 108, and an imaging element 110.

As shown in FIG. 1B, the illumination window 96 and observation window 102 are fixed to the hard distal end portion 22. As shown in FIG. 2, at the proximal end of the illumination window 96, the distal end of the light guide bundle 94 is fixed to the hard distal end portion 22. At the proximal end of the observation window 102, the objective lens 104 is fixed to the hard distal end portion 22. At the proximal end of the objective lens 104, the distal end of the image guide 106 is fixed to the hard distal end portion 22. The light guide bundle 94 and image guide 106 are extended to the operation portion 14 through the bending portion 24 and flexible portion 26.

Figure 6A:
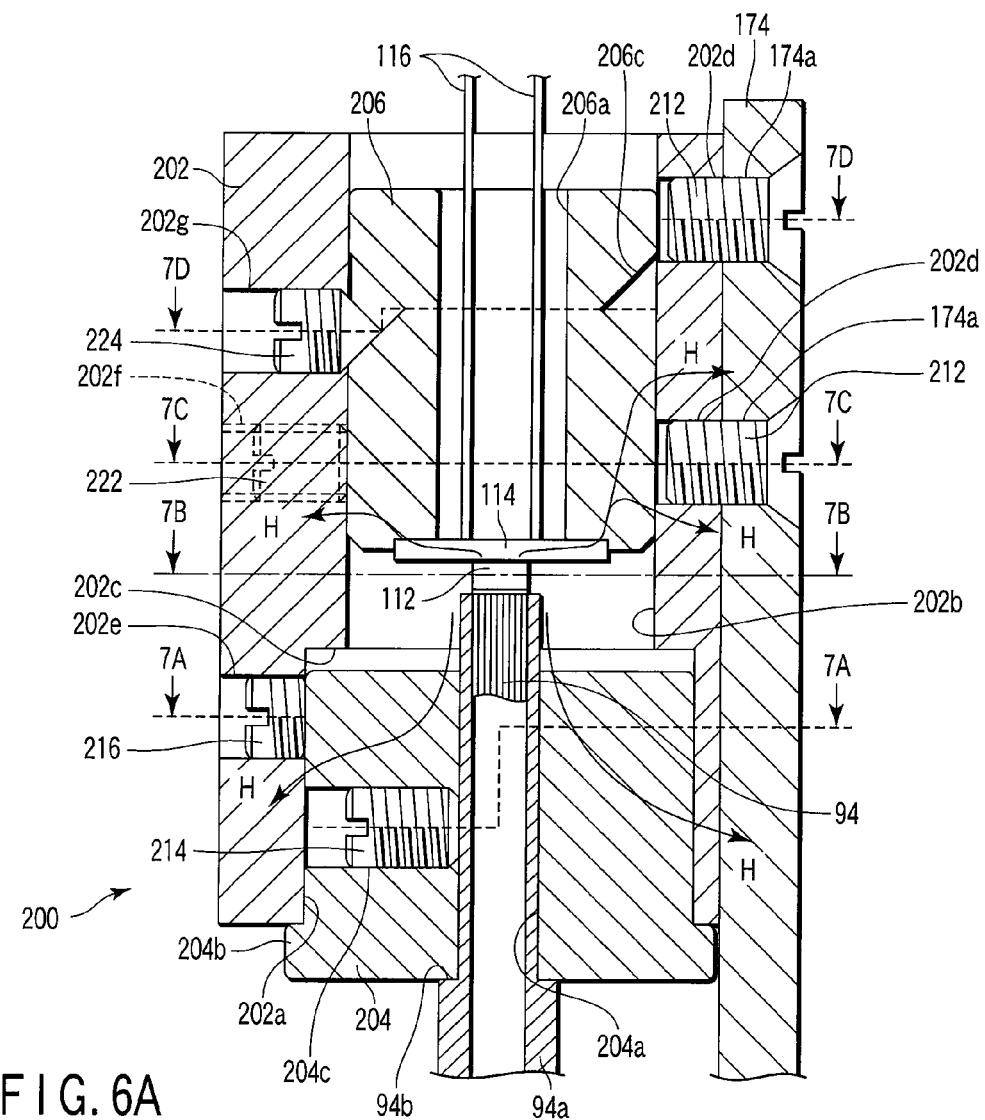
FIG. 6A is a schematic longitudinal sectional view showing a light source apparatus and a connection member to hold the light source apparatus arranged inside the grip part of the operation portion of the endoscope, according to the first embodiment.

In the light guide bundle 94, a number of light guide fibers are collected. The outside of these collected light guide fibers is covered with a protection tube, and is shaped to have a circular cross section. As shown in FIG. 6A, a light guide connector (a heat radiation member of the illumination apparatus) 94a having a step 94b is fixed with an adhesive to the proximal end of the light guide bundle 94. The proximal end face (an illumination light incident surface, or a light-receiving surface) of the light guide bundle 94 is made flush with the proximal end face of the light guide connector 94a, or the proximal end face of the light guide connector 94a is shaped to project further to the proximal end side of the light guide bundle 94. Here, the proximal end faces of the light guide bundle 94 and light guide connector 94a are assumed to be flush with each other.

Figure 6B:
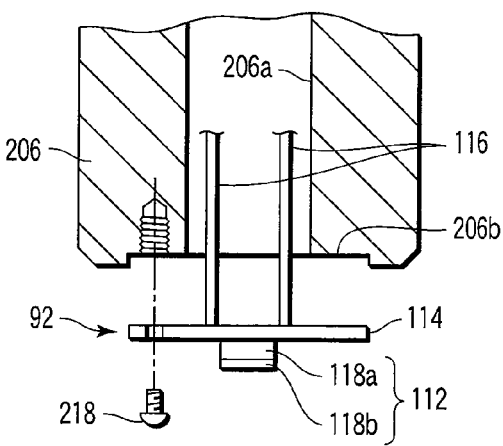
FIG. 6B is a schematic partial longitudinal sectional view showing the state that a mounting substrate provided with a light source is fixed to a second cylindrical member of the connection member.

The light source unit 92 is fixed to the inside of the operation portion 14. The light source unit 92 includes a light source 112, a mounting substrate 114, and a lead wire 116. As shown in FIG. 6B, the light source 112 includes an LED 118a and a fluorescent substance 118b coated on the light-emitting surface of the LED 118a, as an illuminator. The LED 118a is an element to emit blue light, for example. The fluorescent substance 118b is flexible, and made by kneading a flexible resin material with a fluorescent powder. When the LED 118a emits blue light, a yellow fluorescent substance 118b receives the light from the LED 118a, and glows white. Therefore, the light source 112 emits pseudo-white light by applying the blue illumination light of the LED 118a to the fluorescent substance 118b.

The mounting substrate 114 is made of a material with good thermal conductivity such as aluminum nitride of the like, and shaped circular with a small diameter, for example. The LED 118a is mounted at the center axis position one side of the mounting substrate 114. One end of the lead wire 116 is fixed to the other side of the mounting substrate 114. The other end of the lead wire 116 is connected to a power supply control circuit 136, described later (refer to FIG. 2).

As shown in FIG. 6A, the light source 112 is provided in contact with the proximal end of the light guide bundle 94. At this time, the light source 112, light guide bundle 94 and illumination window 96 are optically connected. Therefore, the illumination light emitted by the LED 118a of the light source 112, and turned to pseudo-white light by the fluorescent substance 118b is emitted from the distal end of the insertion portion 12 through the light guide bundle 94 and illumination window 96.

The image-formation lens 108 and imaging element 110 shown in FIG. 2 are fixed to the operation portion main body 32. The image-formation lens 108 is fixed to the proximal end of the image guide 106. The imaging element 110, such as a CCD or CMOS, is fixed at a position where the image-formation lens 108 forms an observation image. At this time, the observation window 102, objective lens 104, image guide 106, image-formation lens 108 and imaging element 110 are optically connected. Therefore, the light emitted from the illumination window 96 and reflected from a subject (an observation object) S (refer to FIG. 2) is imaged by the imaging element 110 through the observation window 102, objective lens 104, image guide 106 and image-formation lens 108. Therefore, an observation image of the subject S can be obtained.

As shown in FIG. 1A and FIG. 2, the operation portion main body 32 is provided with an image display device 34. The outside frame of the image display device 34 is formed by a device main body (cabinet) 122 shaped substantially rectangular parallelepiped (box-shape), and a tilt lever (a finger rest) extended from a corner of one side of the device main body 122 to the front side 10f of the endoscope 10, in a plane. The device main body 122 and tilt lever 124 are formed as one piece. On the front surface of the device main body 122, a monitor 132 for displaying an endoscopic image is provided. The device main body 122 is pivotally supported at the upper end of the operation portion 14. Therefore, the monitor 132 can be inclined to an easy-to-see position for a user of the endoscope 10.

Further, as shown in FIG. 2, the device main body 122 contains a battery 134, a power supply control circuit 136, a recording control circuit 138 having a recording medium such as an internal memory (not shown), a display element control circuit 140, and an imaging element control circuit 142 as a processing circuit.

The battery 134 is connected to the power supply control circuit 136. The power supply control circuit 136 is connected to the monitor 132, recording control circuit 138, display element control circuit 140, and imaging element control circuit 142. Further, the power supply control circuit 136 is also electrically connected to the light source unit 92 and imaging element 110, and supplies power to these parts.

The power supply control circuit 136 receives the power supplied from the battery 134, and outputs a suitable driving power to the light source unit 92, imaging element 110, monitor 132, recording control circuit 138, display element control circuit 140, and imaging element control circuit 142.

The power supply control circuit 136 is provided with a power switch 152, and is turned on/off by operating the power switch 152. The battery 134 employs a rechargeable secondary cell, which can be inserted into and removed from a housing slot, described later.

The recording control circuit 138 is supplied with signals from the image switch 46 provided in the operation portion main body 32 (refer to FIG. 3), and a still image recording switch 156 and a moving image recording switch 158 provided in the image display device 34 (refer to FIG. 1A).

According to the input signals from these switches, the recording control circuit 138 controls recording, playing back and freeze-frame of a signal of an endoscopic image as a still image or a moving image. Namely, the recording control circuit 138 stores an observation image of a subject area S signalized by the imaging element control circuit 142 on a recording medium, and outputs the stored signal to the display element control circuit 140 according to the instructions for playing back and freeze-frame from the image reproducing switch 46b.

The recording control circuit 138 can contain an external recording medium such as an external recording element attachable to/detachable from a housing slot, to be described later, in addition to a recording medium such as an internal memory, described above.

The display element control circuit 140 visualizes a signal from the recording control circuit 138 or the imaging element control circuit 142, and displays an endoscopic image on the monitor 132. The recording control circuit 138 sends an instruction signal to the power supply control circuit 136 to supply power to the light source unit 92, imaging element 110 and imaging element control circuit 142, according to the signals input from the switches 46, 156 and 158.

As shown in FIG. 1A, a power switch 152, a power indicator 154, a still image recording switch 156 and a moving image recording switch 158 are provided on the surface of the device main body 122, in addition to the monitor 132. The power switch 152 is provided on the rear side 10b of the device main body 122. The power indicator 154, still image recording switch 156 and moving image recording switch 158 are provided in the marginal area of the monitor 132, for example. The power switch 152 and power indicator 154 are connected to the power supply control circuit 136. Therefore, the power indicator 154 is turned on when the power switch 152 is turned on, and turned off when the power is turned off.

The still image recording switch 156 and moving image recording switch 158 are connected to the recording control circuit 138. The still image recording switch 156 is pressed to turn on when setting a still image for a recording endoscopic image record a still endoscopic image. The moving image recording switch 158 is pressed to turn on when setting a moving image for a recording endoscopic image record a moving endoscopic image.

The device main body 122 is provided with a housing (not shown), and a cover 162 configured to open and close the housing. The housing is provided with slots for housing the battery 134 and an external recording element (a storage medium) such as a not-shown memory card (e.g., a XD picture card (registered trademark), respectively. The external recording element can transfer data from the internal memory of the recording control circuit 138. The slot for housing the battery 134 is connected to the power supply control circuit 136, and the slot for housing the memory card is connected to the recording control circuit 138. These components provided in the device main body 122 are enclosed with the cover 162, to make them watertight.

An observation image of the subject area S taken by the imaging element 110 is output from the imaging element 110 to the imaging element control circuit 142. The imaging element control circuit 142 converts the observation image of the subject area S taken by the imaging element 110 to a signal, and outputs the signal to the recording control circuit 138 and display element control circuit 140.

As shown in FIG. 4 and FIG. 5A, the operation portion main body 32 and grip part 36 of the operation portion 14 are provided with outer casings 32a and 36a, respectively. These outer casings 32a and 36a are made of so-called engineering plastic (plastic material), which is resistant to chemicals and heat, and is electrically insulated.

The outside of the end portion of the outer casing 32a of the operation portion main body 32 is fixed to the inside of the proximal end portion of the outer casing 36a of the grip part 36, in the state sealed by inserting a sealing member 37 such as an O-ring. Therefore, the insides of the outer casings 32a and 36a are made watertight.

The outer casing 32a of the operation portion main body 32 is provided with the suction button housing 84 and the pivot 42a of the bending control lever 42.

The outer casing 36a of the grip part 36 is shaped cylindrical with a protection hood 38 fixed to the distal end (the insertion portion 12), and the proximal end (close to the operation portion main body 32) is fixed to the outer casing 32a of the operation portion main body 32. Further, the outer casing 36a of the grip part 36 is provided with a cylindrical extension 36b to place a connection tube 78 and treatment device insertion port 80.

To the inside of the outer casing 32a of the operation portion main body 32, a first frame (intermediate plate) 172 made of a metallic material with a large thermal capacity and good thermal conductivity, such as aluminum is fixed. To the inside of the first frame 172, a second frame 174, made of a metallic material with a large thermal capacity and good thermal conductivity, such as aluminum, like the first frame 172, is fixed. The second frame 174 is provided inside the outer casing 36a of the grip part 36. Particularly, the second frame 174 is extended from the distal end (close to the insertion portion 12) of the grip part 36 to the proximal end (close to the operation portion main body 32), along the front side 10f and rear side 10b of the outer casing 36a, for example. The second frame 174 is divided into two or more parts, for example a pair, and formed discontinuously including a notch (refer to FIGS. 7A to 7D). The second frame 174 is not limited to a symmetrical form, and may be any form that fits the shape of the outer casing 36a.

Each second frame 174 is fixed with a screw 173 to the first frame 172 fixed to the inside of the outer casing 32a of the operation portion main body 32. In the side of the second frame 174 close to the insertion portion 12, the branch part 76, at which the channel 62 and treatment device insertion port 80 are joined, is fixed tightly to the second frame 174 with a not-shown screw.

As shown in FIG. 5A, the branch part 76 includes first to third connectors 76a, 76b and 76c. The first connector 76a is connected to the proximal end of the channel tube 74 which is inserted into the insertion portion 12 and opened at the distal end of the insertion portion 12. The second connector 76b of the branch part 76 is disposed inside the second frame 174. The third connector 76c of the branch part 76 is connected to the connection tube 78 in being strongly pressed to the third connector 76c of the branch part 76 by the force of a nut 79a tightened to the inside surface of the extension 36b. Further, the treatment device insertion port 80 is fixed to the connection tube 78 with a screw.

The treatment device insertion port 80 and the extension 36b of the outer casing 36a are constructed watertight to prevent ingress of liquid by using a sealing member 79b such as an O-ring.

The treatment device insertion port 80 includes a cylindrical part (opening) 80a exposed to the outside from the extension 36b of the outer casing 36a in the part exceeding the area to be held by an operator (near the proximal end of the insertion portion 12). This cylindrical part 80a is a part to dissipate heat to the outside.

A flange 80b is formed projecting outward, at the end portion of the cylindrical part 80a of the treatment device insertion port 80. A forceps plug 190 is attachable to and detachable from the treatment device insertion port 80, as shown in FIG. 3.

At the distal end of the second frame 174, first and second connection members 176a and 176b are disposed.

The first connection member 176a is connected to the second frame 174 with a screw 177a. The first connection member 176a connects the second frame 174 to the flexible portion 26 of the insertion portion 12. Namely, the first connection member 176a is fixed so that the inside surface of the first connection member 176a contacts the outside surface of the connector 26a at the proximal end portion of the flexible portion 26 of the insertion portion 12.

The inside surface of the first connection member 176a and the outside surface of the connector 26a at the proximal end of the flexible portion 26 are made watertight to prevent ingress of liquid, by using a sealing member 26b such as an O-ring. The outer casing member 36a and first connection member 176a are made watertight to prevent ingress of liquid by using the sealing member 177c such as an O-ring, for example.

The rubber protection hood 38 is formed on the outside surface of the second connection member 176b as one piece. The outside of the first connection member 176a is screwed into the inside of the second connection member 176b.

The first frame 172, second frame 174, branch part 76, connection tube 78, treatment device insertion port 80, connection members 176a and 176b, and connector 26a of the flexible portion 26 are made of metallic materials with a large thermal capacity and good thermal conductivity, such as aluminum. The members to serve as liquid flow paths denoted by the reference numbers 76, 78 and 80 (refer to FIG. 5A) may be made of metallic materials with resistance to corrosion, such as stainless steel.

As shown in FIG. 3 and FIG. 5B, a forceps plug 190 is detachably attached to the treatment device insertion port 80. As shown in FIG. 5B, the forceps plug 190 includes a cylindrical outer casing 192, and first and second rubber valves 194 and 196 provided inside the outer casing 192. The outer casing 192 and the first and second rubber valves 194 and 196 are made of insulation materials.

The first and second rubber valves 194 and 196 are provided in being overlapped in the outer casing 192. The first rubber valve 194 is made to be in contact with the distal end of the outer casing 192. The first rubber valve 194 has a slit 194a. The second rubber valve 196 is provided with a circular opening 196a, for example, to insert a treatment device (not shown). When a treatment device is not inserted, ends formed by the slit 194a of the first rubber valve 194 are abutted, and the inside of the forceps plug 190 is hermetically sealed. When a treatment device is inserted, the inside edge portions of the opening 196a of the second rubber valve 196 securely contact each other, and the inside of the forceps 190 is hermetically sealed.

The outer casing 192 of the forceps plug 190 can engage with the flange 80b of the treatment device insertion port 80. The proximal end portion of the outer casing 192 is flared. Namely, the end portion of the cylindrical main body is enlarged. Therefore, the treatment device insertion port 80 has a clearance $S_2$ to the internal surface of the proximal end portion of the outer casing 192 of the forceps plug 190. The heat H transmitted to the treatment device insertion port 80 is radiated from the clearance $S_2$.

When the forceps plug 190 is fitted in the treatment device insertion port 80, a projection 192a of the inside surface of the plastic outer casing 192 of the forceps plug 190 is elastically deformed, and the forceps plug 190 is pushed in until it rides over the flange 80b of the treatment device insertion port 80. As shown in FIG. 5B, when the forceps plug 190 is completely fitted in the treatment device insertion port 80, the inside of the path is closed to the outside (outside air) with two rubber valves 194 and 196.

When a forceps or the like is inserted into the channel tube 74, the distal end of the forceps is inserted into the slit (entrance) 194a of the first rubber valve 194 of the forceps plug 190, and inserted further while being deformed through close contact with the inside edge portions of the opening 196a of the second rubber valve 196.

Even after the forceps plug 190 is completely fitted in the treatment device insertion port 80, the end portion of the outer casing 192 of the forceps plug 190 does not contact the extension 36b of the outer casing 36a of the grip part 36, and the connection of the cylindrical part 80a of the treatment device insertion port 80 to the outside is ensured. Namely, the clearance $S_2$ is ensured.

Next, an explanation will be given on a structure to connect the light source unit 92 and light guide bundle 94 of the illumination optical system 64 to the operation portion 14, with reference to FIG. 4 and FIGS. 6A to 7D.

A space $S_1$ is formed between the second frame 174 and the inside surface of the outer casing 36a of the grip part 36. The space $S_1$ gives heat insulation to prevent the heat H in the first frame 172, second frame 174, branch part 76, connection tube 78, treatment device insertion port 80, connection members 176a and 176b, and connector 26a of the flexible portion 26, from being transmitted to the outside of the outer casing 36a.

In the space between the opposing second frames 174 inside the grip part 36, the suction path 82 of the channel 62, the image guide 106 of the observation optical system 66, the bending operation wire 52, and the light source unit 92 and the light guide bundle 94 of the illumination optical system 64 are extended. Namely, the light source unit 92 includes the lead wire 116 extended from the power supply control circuit 136 to the mounting substrate 114 (refer to FIG. 6A) in the grip part 36, to transmit the power supplied from the battery 134 to the mounting substrate 114 of the light source unit 92.

In the space between the opposing second frames 174, the connection member 200, which optically and thermally connects the light source unit 92 and light guide bundle 94, is provided. Therefore, the connection member 200 is used also as a heat transmission frame or a heat radiation frame. Concretely, the connection member 200 is fixed closely contacting the internal surface of the second frame 174. Namely, the connection member 200 is provided to securely transmit the illumination light from the light source 112 to the light guide bundle 94, and effectively diffuse the heat generated from the light source 112 upon emission of light, by using the second frame 174.

The connection member 200 includes a tubular body 202, and first and second cylindrical members 204 and 206 provided inside the tubular body 202. The tubular body 202, first cylindrical member 204 and second cylindrical member (holding part) 206 are made of a material having a large thermal capacity and good thermal conductivity (e.g., a metal, such as aluminum).

Figure 7A:
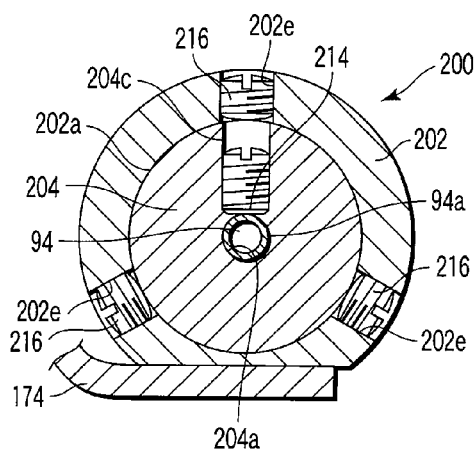
FIG. 7A is a schematic transverse sectional view along line 7A-7A in FIG. 6A of the light source apparatus and the connection member to hold the light source arranged inside the grip part of the operation portion of the endoscope, according to a first embodiment.
Figure 7B:
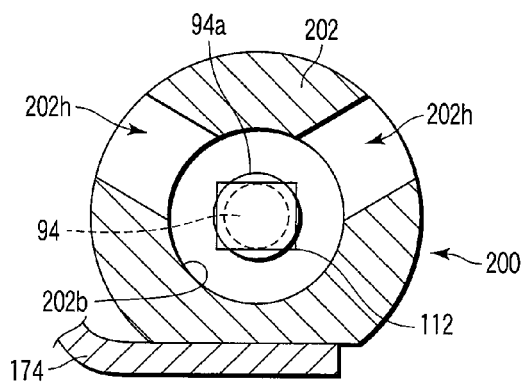
FIG. 7B is a schematic transverse sectional view along line 7B-7B in FIG. 6A.
Figure 7C:
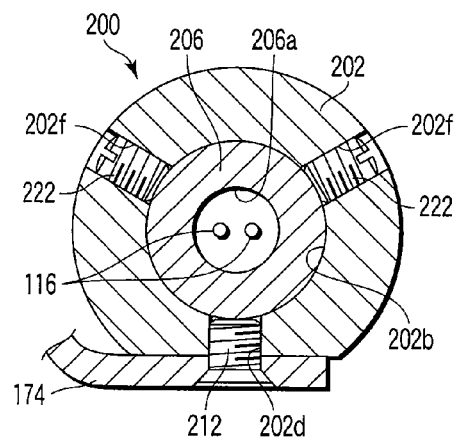
FIG. 7C is a schematic transverse sectional view along line 7C-7C in FIG. 6A.
Figure 7D:
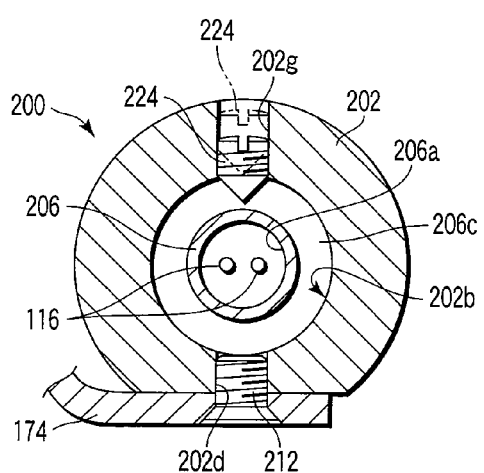
FIG. 7D is a schematic transverse sectional view along line 7D-7D in FIG. 6A.

As shown in FIG. 6A, FIG. 7C and FIG. 7D, screw holes 174a and 202d are formed in the frame 174 of the grip part 36 of the operation portion 14 and the tubular part 202, respectively. By inserting a screw 212 into the screw holes 174a and 202d, the frame 174 of the grip part 36 is fixed to the tubular part 202 of the connection member 200.

As shown in FIGS. 7A to 7D, the outside surface of the cross section of the tubular part 202 is substantially U-shaped. Therefore, a rectangular plane is formed on the outside surface of the tubular part 202. The tubular part 202 contacts the frame 174 in its rectangular plane, and is positioned in a predetermined state.

Inside the tubular part 202, first and second openings 202a and 202b with different inside diameters are formed. The first opening 202a is provided at one end of the tubular part 202 (the side close to the distal end portion of the insertion portion 12), and the second opening 202b is provided at the other end (the side separated from the distal end portion of the insertion portion 12). The first and second openings 202a and 202b are substantially cylindrical spaces formed in the state connected to the inside of the tubular part 202. Therefore, a step height 202c is formed at the boundary between the first opening 202a and second opening 202b. The centerlines of the first and second openings 202a and 202b are preferably on the same axis.

As shown in FIG. 6A and FIG. 7A, the first cylindrical member 204 has a cylindrical through hole 204a at the center, and a flange 204b at one end. The first cylindrical member 204 has a screw hole 204c formed from the side to the center of the through hole 204a.

As the flange 204b contacts one end of the tubular part 202, the first cylindrical member 204 is fixed in being positioned to the tubular part 202 when placed in the first opening 202a. The light guide connector 94a covered with the light guide bundle 94 is fixed to the through hole 204a of the first cylindrical member 204 with a screw 214 provided in the screw hole 204c penetrating the first cylindrical member 204 sideways. As the light guide connector 94a has the step 94b, the light guide connector 94a is fixed at a predetermined position with respect to the first cylindrical member 204.

The first cylindrical member 204 with the light guide connector 94a fixed as above is disposed in the first opening 202a of the tubular part 202, and fixed with a screw 216 provided in the screw hole 202a penetrating the tubular part 202 sideways.

As shown in FIGS. 6A and 6B, the second cylindrical member 206 has a cylindrical through hole 206a at the center, and a recess 206b to hold the mounting substrate 114 at one end. The recess 206b is formed to fit the mounting substrate 114. Therefore, the mounting substrate 114 is fitted in the recess 206b, and the mounting substrate 114 is fixed to the recess 206b with a screw 218. Namely, the light source unit 92 is fixed to the second cylindrical member 206. The lead wire 116 extended from the mounting substrate 114 is extended from the proximal end of the second cylindrical member 206 through the inside of the through hole 206a of the second cylindrical member 206.

The second cylindrical member 206 with the light source unit 92 fixed as above is disposed in the second opening 202b of the tubular part 202, and fixed with screws 222 and 224 provided in screw holes 202f and 202g penetrating the tubular part 202 sideways.

At this time, on the side of the second cylindrical member 206, a lengthwise position adjustment groove is formed circularly in the circumferential direction as shown in FIG. 6A and FIG. 7D. The cross section of the circumferential groove 206c is substantially V-shaped as shown in FIG. 6A. The screw hole 202g and circumferential groove 206c are connected. Therefore, in the circumferential groove 206c, a screw 224 having a conical or truncated conical distal end sharpened to substantially the same inclination angle as the circumferential groove 206c is inserted through a screw hole 202g penetrating the side of the second cylindrical member 206.

As the distal end of the screw 224 is gradually projected, the second cylindrical member 206 is moved close to the first cylindrical member 204. Namely, the fluorescent substance 118b of the light source 112 is pressed to the proximal end portions of the light guide bundle 94 and light bundle guide connector 94a, which are flush with each other.

In this state, as shown in FIG. 6A and FIG. 7C, the second cylindrical member 206 is fixed with a screw 222 provided in a screw hole 202f penetrating the tubular part 202 sideways.

The LED 118a of the light source 112 is usually formed as a rectangular parallelepiped. Therefore, as shown in FIG. 7B, the LED 118a has a rectangular cross section in this embodiment. The light-emitting surface of the LED 118a is coated with the fluorescent substance 118b. Here, the light-emitting surface of the light source 112 includes one or both of the light-emitting surface of the LED 118a itself and the illumination light-emitting surface formed by coating the fluorescent substance 118b on the LED 118a.

The light guide connector 94a is cylindrical in this embodiment. The outside diameter of the light guide bundle 94 contacts a pair of long sides of two pairs of sides of the rectangular fluorescent substance 118b formed (coated) on the rectangular LED 118a. Therefore, illumination light can be applied to the whole surface of the proximal end face of the cylindrical light guide bundle 94 covered by the cylindrical light guide connector 94a. As the light guide bundle 94 is provided as above with respect to the light source 112, the light guide bundle 94 is provided with a part of the proximal end face of the light guide connector 94a projected from the light-emitting surface of the fluorescent substance 118b. The light guide connector 94a is provided on the outside of the light guide bundle 94, and the fluorescent substance 118b directly contacts the light guide bundle 94 and light guide connector 94a, except at four corners. Namely, the light guide connector 94a has a part directly contacting the light source 112 (a tangential part α (refer to FIG. 10A), and a part projecting from the light source 112 (a non-tangential part β) (refer to FIG. 10A).

As shown in FIG. 7B, the tubular part 202 has a confirmation hole 202h connecting from the side to the center axis of the second opening 202b. The confirmation hole 202h is a window for confirming the state of contact (tight contact) between the light source 112, light guide bundle 94 and light guide connector 94a. Therefore, it is possible to confirm that the light source 112, light guide bundle 94 and light guide connector 94a are optically and thermally connected by aligning the optical axes in the connection member 200, by checking visually or by using a not-shown small scope.

Next, an explanation will be given on the function of the endoscope 10 according to this embodiment.

When the power switch 152 is turned on, power is supplied from the battery 134 to the light source unit 92, and the LED 118a of the light source 112 emits light. As the fluorescent substance 118b is coated on the light-emitting surface of the LED 118a, the light source 112 emits a pseudo-white light to the proximal end face of the light guide bundle 94 as an illumination light. The illumination light is emitted through the light guide bundle 94 and illumination window 96. Therefore, an image emitted to the observation optical system 66 is displayed on the monitor 132.

As observation is continued, the LED 118a is heated as time passes. The heat H generated from the LED 118a itself is transmitted to the second cylindrical member 206 through the mounting substrate 114 with good thermal conductivity. As the mounting substrate 114 and second cylindrical member 206 are made of materials with large thermal capacity, the heat H is diffused during transmission to the mounting substrate 114 and second cylindrical member 206.

Further, as shown in FIG. 7B, the proximal end face of the light guide connector 94a has a contact part directly contacting the fluorescent substance 118b, and a non-contact part located outside the fluorescent substance 118b.

A part of the proximal end face of the light guide connector 94a contacts the light-emitting surface of the light source 112. Therefore, the light guide connector 94a absorbs the heat H generated from the light source 112 itself, through the proximal end face. The heat H absorbed through the proximal end face of the light guide connector 94a is transmitted to the distal end face of the light guide connector 94a, and is partially diffused during transmission. At this time, the heat H is also diffused from the non-contact part of the proximal end face of the light guide connector 94a located outside the light source 112.

As the heat H is diffused also from the non-contact part, the light guide connector 94a itself is prevented from increasing in temperature. This prevents deterioration of the adhesive bonding the light guide bundle 94 to the light guide connector 94a.

As the light guide connector 94a is tightly fixed to the first cylindrical member 204, in the part close to the distal end side rather than the proximal end face, the heat H absorbed by the light guide connector 94a is transmitted to the first cylindrical member 204. As the first cylindrical member 204 is made of material with large thermal capacity, the heat H is diffused during transmission to the first cylindrical member 204.

The first and second cylindrical members 204 and 206 are fixed to the tubular part 202. Therefore, the heat H transmitted to the first and second cylindrical members 204 and 206 is transmitted to the tubular part 202.

As the tubular part 202 is fixed to the second frame 174 with good thermal conductivity, the heat H is transmitted to the second frame 174. As the tubular part 202 contacts the second frame 174 in a plane, the heat H is efficiently transmitted from the tubular part 202 to the second frame 174.

Therefore, the heat H generated while the light source 112 is emitting light is transmitted through not only the mounting substrate 114, but also the light guide connector 94a directly contacting the light-emitting surface of the light source 112. Namely, the heat H generated when the light source 112 emits light is transmitted and diffused through two or more paths.

The heat H transmitted to the second frame 174 is radiated through the branch part 76, connection tube 78 and treatment device insertion port 80. Therefore, the heat H generated when the light source 112 emits light is radiated through the treatment device insertion port 80.

As the tubular part 202, second frame 174, branch part 76, connection tube 78 and treatment device insertion port 80 are made of materials with large thermal capacity, the heat H is diffused during transmission.

As explained above, this embodiment provides the following effects.

The heat H generated when the light source 112 emits light is transmitted and radiated through at least two paths: one path transmits the heat to the tubular part 202 through the mounting substrate 114 and second cylindrical member 206, and the other path transmits the heat to the tubular part 202 through the light guide connector 94a and first cylindrical member 204.

While the light source 112 is emitting light, the heat H is gradually transmitted through two or more paths, and diffused at the same time. Therefore, the light-emitting efficiency of the light source 112 is not decreased by the heat H, and the light-emitting efficiency is kept high. Further, as the heat H generated from the light source 112 is gradually transmitted and diffused, degradation of the LED 118a of the light source 112 can be delayed, and the life of the LED 118a can be prolonged.

Further, as the proximal end face of the light guide connector 94a is provided with a non-contact part in addition to a contact part directly contacting the light-emitting surface of the light source 112, the light guide connector 94a itself absorbs heat and prevents the LED 118a from temperature increase. This prevents deterioration of the adhesive used between the light guide bundle 94 and light guide connector 94a.

As the outside surface of the tubular part 202 is substantially D-shaped, the tubular part 202 has a plane on the outside surface. The tubular part 202 is fixed to the frame 174 with the plane part contacting the frame. Therefore, the connection member 200 and frame 174 contact over a broad area. Therefore, the heat H can be efficiently transmitted from the connection member 200 to the frame 174.

As the fluorescent substance 118b contacts the proximal end faces of the light guide bundle 94 and light guide connector 94a, it prevents from forming an air layer between the fluorescent substance 118b and the light guide bundle 94. The center axes of the fluorescent substance 118b and light guide bundle 94 are substantially aligned. Therefore, the pseudo-white light emitted from the LED 118a through the fluorescent substance 118b is efficiently applied to the proximal end face of the light guide bundle 94 with minimized incident loss caused by diffused reflection, and guided to the distal end face.

According to the above first embodiment, the following can be said.

The illumination apparatus includes a light source 112 to generate heat when emitting illumination light from a light-emitting surface, a light guide bundle (light transmission member) 94, and a light guide connector (heat radiation member) 94a. The light guide bundle 94 has a light-receiving surface (the proximal end face of the light guide bundle 94), which opposes the light-emitting surface of the light source 112, and receives the illumination light emitted from the light-emitting surface of the light source 112, and guides the illumination light from the light source 112 received on the light-receiving surface. The light guide connector 94a has an end face which is arranged along the light guide bundle 94 and opposed to the light-emitting surface of the light source 112, and a contact part α which partially contacts the light-emitting surface of the light source 112, and transmits the heat of the light source 112. In this case, as the light-emitting surface of the light source 112 directly contacts the light guide connector 94a, the heat generated by lighting of the light source 112 can be directly transmitted to the light guide connector 94a (the heat generated by lighting of the light source is directly absorbed by the light guide connector 94a). As the heat generated in the light source 112 is efficiently transmitted by transmitting to the light guide connector 94a as described above, the heat transmitted to the light guide connector 94a can be diffused through the light guide connector 94a itself.

The end face of the light guide connector 94a of the illumination apparatus also has a non-contact part β located outside the light-emitting surface of the light source 112 (a part extended off the light source 112), in addition to the contact part α. As the light guide connector 94a has a non-contact part β not contacting the light-emitting surface of the light source 112, the heat transmitted directly to the contact part α contacting the light-emitting surface can be radiated by transmitting to the non-contact part β.

The light source 112 of the illumination apparatus is mounted on the mounting substrate 114, which is electrically connected to the opposite side of the light-emitting surface, and is given thermal conductivity. Therefore, the heat from the light source 112 can be diffused by efficiently transmitting the heat not only to the light guide connector 94a, but also to the mounting substrate 114.

In this embodiment, the first cylindrical member 204 fixed to the light guide connector 94a is explained as a member separated from the tubular part 202. It is also possible for the first cylindrical member 204 to be formed as one piece with the tubular part 202.

Further, in this embodiment, the heat H generated in the light source 112 is radiated by transmitting the heat to the treatment device insertion port 80 by using the endoscope 10. The heat H can be diffused before reaching the treatment device insertion port 80. Therefore, as explained in this embodiment, it is not always necessary to provide a part exposed to the outside air in the illumination apparatus provided inside the operation portion 14 of the endoscope 10.

Embodiment 2

A second embodiment will be explained by using FIG. 8. This embodiment is a modification of the first embodiment. The same members as in the first embodiment are given the same reference numerals, and a detailed explanation on these members will be omitted.

Figure 8:
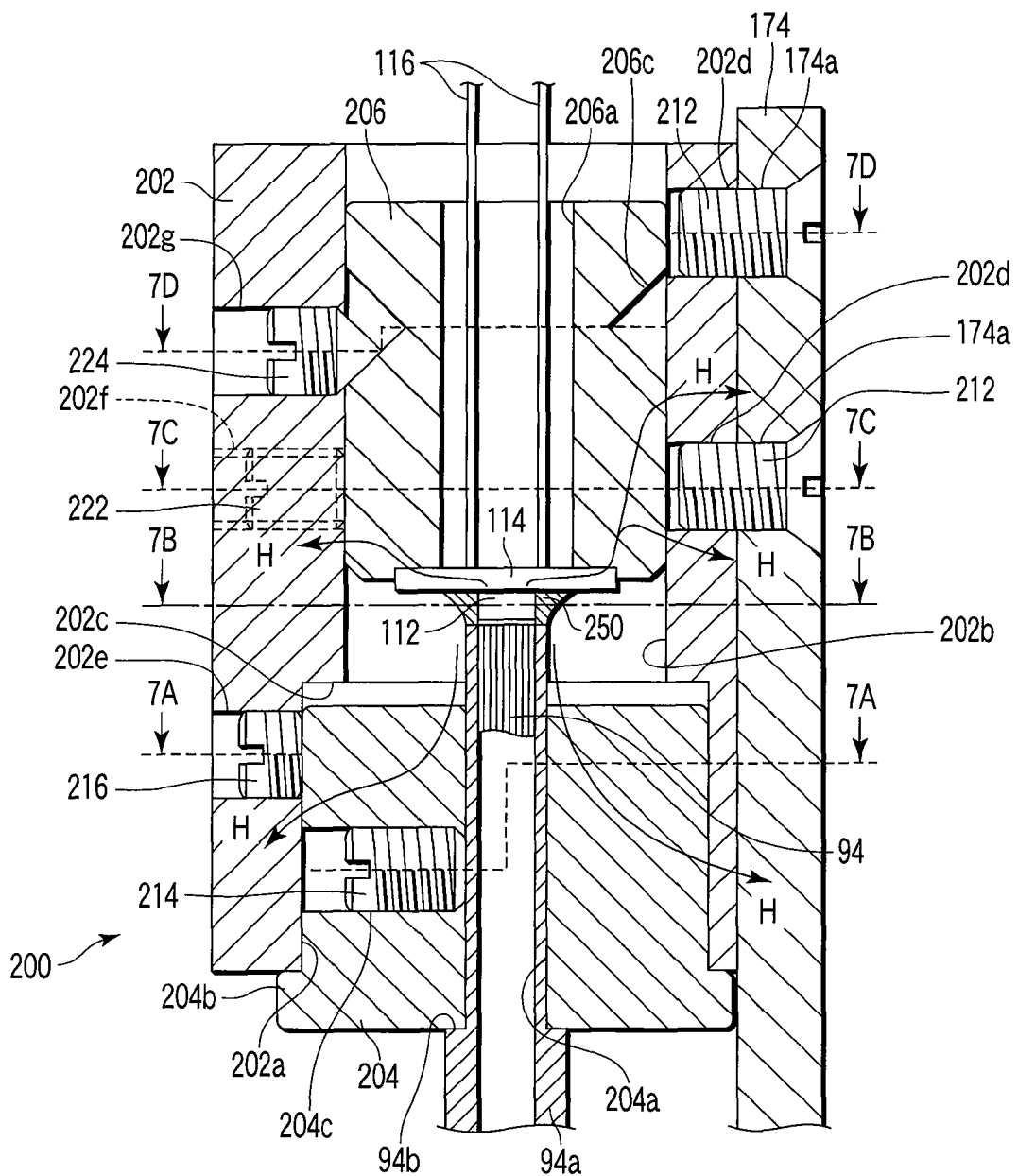
FIG. 8 is a schematic longitudinal sectional view showing the light source and the connection member to hold the light source apparatus arranged inside the grip part of the operation portion of the endoscope, according to a second embodiment.

As shown in FIG. 8, the outside surface of the light source 112 is coated with an adhesive (heat-radiating resin material) 250 having an insulating property and thermal conductive property (radiation property), or an adhesive (resin material) 250 kneaded with a material having an insulating property and good thermal conductivity. Namely, the light source 112 is fixed in contact with the light guide connector 94a with the adhesive 250 of thermal conductivity.

By connecting the mounting substrate 114 and light guide connector 94a with the adhesive 250, a heat transmission path is newly formed between the mounting substrate 114 and light guide connector 94a. Therefore, the path to transmit the heat H from the side of the light source 112 to the light guide connector 94a and mounting substrate 114 is created, the heat H generated by the LED 118a of the light source 112 can be radiated more efficiently. Further, the heat H intercommunicates between the mounting substrate 114 and the light guide connector 94a through the adhesive 250, so that the adhesive 250, mounting substrate 114 and light guide connector 94a are in the thermal equilibrium. This prevents unbalanced heat transmission, in which the heat is transmitted only to one of the mounting substrate 114 and light guide connector 94a.

Embodiment 3

A third embodiment will be explained by using FIGS. 9A and 9B. This embodiment is a modification of the first and second embodiments. The same members as in the first and second embodiments are given the same reference numerals, and detailed explanation on these members will be omitted.

Figure 9A:
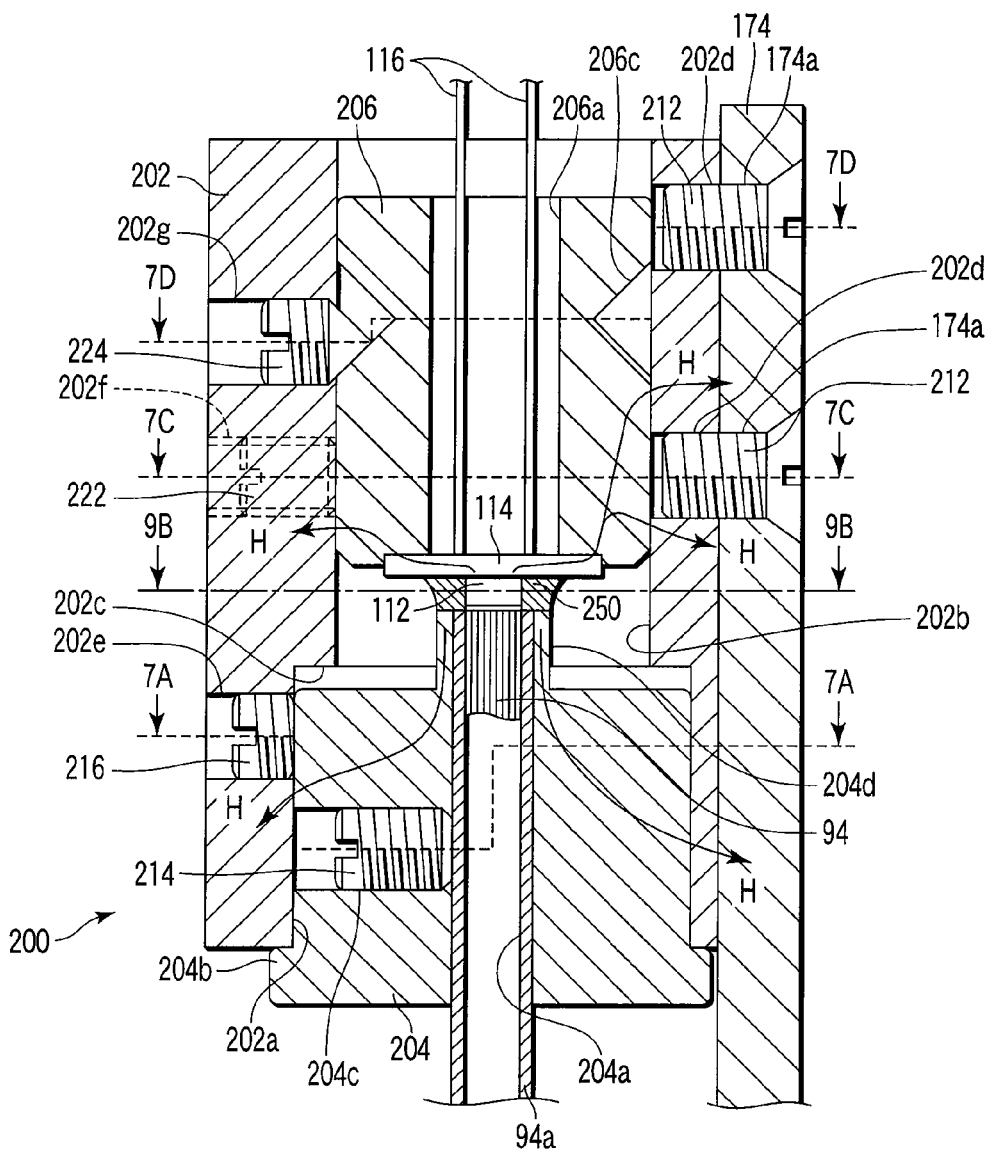
FIG. 9A is a schematic longitudinal sectional view showing the light source and the connection member to hold the light source apparatus arranged inside a grip part of the operation portion of the endoscope, according to a third embodiment.

As shown in FIG. 9A, the light guide connector 94a is shaped like a pipe without the step 94, unlike the light guide connector 94a of the first and second embodiments (refer to FIG. 6A). Therefore, the light guide connector 94a is made thinner than the light guide connector 94a explained in the first and second embodiments.

The first cylindrical member 204 of the connection member 200 includes a cylindrical part (a member serving as a heat transmission member and a heat radiation member of the illumination apparatus) 204d formed in one piece, in the side opposite to the side provided with the flange 204b. The inside surface of the cylindrical part 204d is closely adhered to the outside surface of the light guide connector 94a with an adhesive with thermal conductivity. The proximal end faces of the light guide bundle 94, the light guide connector 94a and the cylindrical part 204d of the first cylindrical member 204 are aligned at the same level.

Figure 9B:
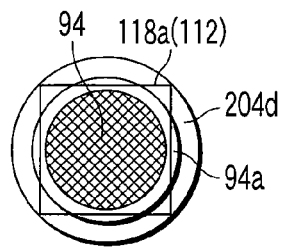
FIG. 9B is a schematic transverse sectional view along line 9B-9B in FIG. 9A.

In contrast, as shown in FIG. 9B, the LED 118a of the light source 112 has a substantially square cross section, the proximal end face of the light guide bundle 94 is housed inside the light source 112. The light guide connector 94a is mostly housed inside the light source 112, but is partially exposed outside the light source 112. The outside surface of the cylindrical part 204d covers the whole light source 112, and contacts the four corners of the light source 112, respectively.

As explained herein, this embodiment provides the following effects. Though an explanation is omitted, this embodiment provides the same effects as described in the first and second embodiment.

By forming the light guide connector 94a thin, the outside diameter of the light guide connector 94a can be made small, and the light guide bundle 94 and light guide connector 94a can be easily inserted into the insertion portion 12. This provides ease of assembling when inserting the light guide bundle 94 and light guide connector 94a into the endoscope 10.

Further, as the light guide connector 94a is made thin, the contact area of the proximal end portion of the light guide connector 94a with the light source 112 is decreased. However, by covering the light guide connector 94a with the cylindrical part 204d used as a member serving as a heat transmission member and a heat radiation member, as in the light guide connector 94a explained in the first and second embodiments, the heat transmission effect of the light guide connector 94a can be compensated for by the cylindrical part 204d. Therefore, the heat H can be transmitted and diffused (radiated) as explained in the first and second embodiments. Besides, as the cylindrical part 204d of the first cylindrical member 204 having good thermal conductivity and large thermal capacity directly contacts the fluorescent substance 118b of the light source 112, the heat radiation effect of the light source 112 can be greatly increased.

In the light-emitting surface of the light source 112, all areas except the part (the light-receiving surface) contacting the proximal end face of the light guide bundle 94 (all areas of the light emitting surface of the light source 112 not used for illumination) contact the proximal end faces of the light guide connector 94a and cylindrical part 204d. Therefore, the part contacting the proximal end faces of the light guide connector 94a and cylindrical part 204d can be used as a heat radiation surface to radiate the heat H generated in the light source 112. Therefore, by arranging the light source 112, light guide connector 94a and cylindrical part 204d as shown in FIG. 9B, the effect of radiating the heat H generated by the light source 112 can be increased.

Embodiment 4

A fourth embodiment will be explained by using FIGS. 10A and 10D. A detailed explanation will be given on the relationship between the light-emitting surface of the light source 112, the proximal end face of the light guide bundle 94 and the proximal end face of the light guide connector 94a explained in the first to third embodiments, by using some examples. The same members as in the first to third embodiments are given the same reference numerals, and a detailed explanation on these members will be omitted.

In the following first to fourth examples, the cylindrical part 204d explained in the third embodiment will not be explained or illustrated. No explanation or illustration will be given also for the case that the cylindrical part 204d is provided outside the light guide connector 94a.

EXAMPLE 1

Figure 10A:
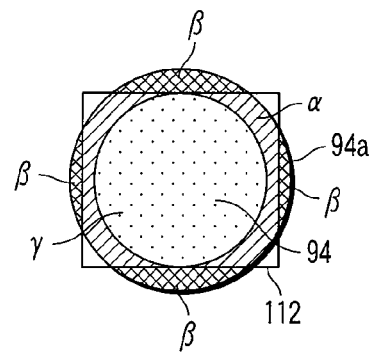
FIG. 10A is a schematic diagram showing an Example 1 of a relationship among a light-emitting surface of a light source of an illumination apparatus, a proximal end face of a light guide bundle, and a proximal end face of a light guide connector, according to the fourth embodiment.

As shown in FIG. 10A, the light-emitting surface of the light source 112 is rectangular (substantially, a square). The proximal end face of the light guide bundle 94 is circular. The proximal end face of the light guide connector 94a is annular. The length of one side of the light source 112 is substantially the same as the diameter of the proximal end face of the light guide bundle 94. The point at which the diagonal lines of the light-emitting surface cross substantially coincides with the centers of the proximal end faces of the light guide bundle 94 and light guide connector 94a.

The proximal end face of the light guide connector 94a has a contact part α to contact the light-emitting surface of the light source 112, and a non-contact part β located outside the light-emitting surface of the light source 112. The proximal end face of the light guide bundle 94 has an illumination light incident part γ to contact the light-emitting surface of the light source 112. The illumination light incident part γ of the light guide bundle 94 contacts the opposing long sides of the rectangular light-emitting surface of the light source 112.

EXAMPLE 2

Figure 10B:
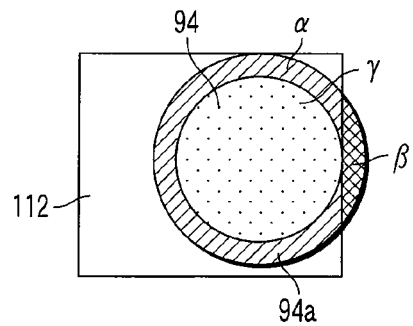
FIG. 10B is a schematic diagram showing an Example 2 of a relationship among the light-emitting surface of the light source of the illumination apparatus, the proximal end face of the light guide bundle, and the proximal end face of the light guide connector, according to the fourth embodiment.

As shown in FIG. 10B, as in the first example, the light-emitting surface of the light source 112 is rectangular, the proximal end face of the light guide bundle 94 is circular, and the proximal end face of the light guide connector 94a is annular. The length of a short side of the light source 112 is made a little longer than the diameter of the proximal end face of the light guide connector 94a. The outside surface of the light guide bundle 94 contacts one of a pair of short sides of the light source 112, and the outside surface of the light guide connector 94a contacts one of a pair of long sides of the light source 112. A part of the light guide connector 94a is a non-contact part β located outside the light-emitting surface of the light source 112.

EXAMPLE 3

Figure 10C:
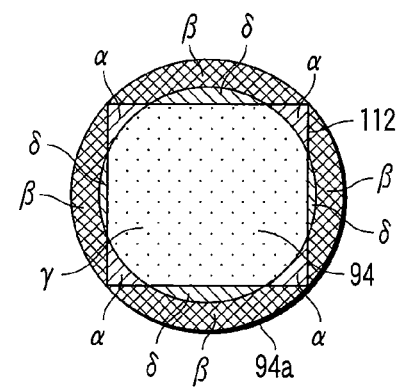
FIG. 10C is a schematic diagram showing an Example 3 of a relationship among the light-emitting surface of the light source of the illumination apparatus, the proximal end face of the light guide bundle, and the proximal end face of the light guide connector, according to the fourth embodiment.

As shown in FIG. 10C, as in the first and second examples, the light-emitting surface of the light source 112 is rectangular (substantially, a square), the proximal end face of the light guide bundle 94 is circular, and the proximal end face of the light guide connector 94a is annular. The length of each side of the light source 112 is smaller than the diameter of the light guide bundle 94. The point at which the diagonal lines of the light-emitting surface cross substantially coincides with the centers of the proximal end faces of the light guide bundle 94 and light guide connector 94a.

The proximal end face of the light guide connector 94a includes a contact part α and a non-contact part β with respect to the light-emitting surface of the light source 112. The proximal end face of the light guide bundle 94 has an illumination light incident part γ to contact the light-emitting surface of the light source 112, and an illumination light not-incident part δ located outside the light-emitting surface of the light source 112. The four corners of the light source 112 contact the outer periphery of the proximal end face of the light guide connector 94a.

EXAMPLE 4

Figure 10D:
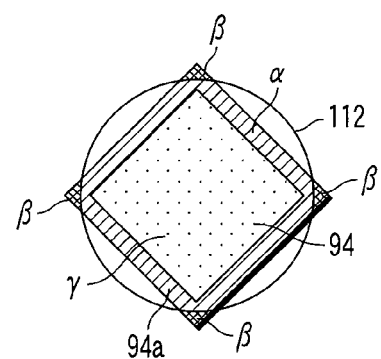
FIG. 10D is a schematic diagram showing an Example 4 of a relationship among the light-emitting surface of the light source of the illumination apparatus, the proximal end face of the light guide bundle, and the proximal end face of the light guide connector, according to the fourth embodiment.

As shown in FIG. 10D, unlike in the first to third examples, the light-emitting surface of the light source 112 is circular, the proximal end face of the light guide bundle 94 is square (rhombus), and the proximal end face of the light guide connector 94a is rectangular and annular. The length of a diagonal line of the proximal end face of the light guide bundle 94 is made smaller than the diameter of the light source 112. The length of a diagonal line of the proximal end face of the light guide connector 94a is made a little longer than the diameter of the light source 112. The center of the light source 112 substantially coincides with the point at which the diagonal lines of the proximal end faces of the light guide bundle 94 and light guide connector 94a cross each other.

In the first to fourth example, when the proximal end faces of the light guide bundle 94 and light guide connector 94a contact the light-emitting surface of the light source 112, the light guide connector 94a includes a contact part α where at least a part of the light guide connector 94a contacts the light-emitting surface of the light source 112, and a non-contact part β where at least a part of the light guide connector 94a is located outside the light-emitting surface of the light source 112. Therefore, the contact part α absorbs the heat H generated in the light source 112. However, as the non-contact part β contacts air or the adhesive 250 inside the grip part 36 of the operation portion 14, the non-contact part β contributes to diffuse the heat H from the contact part α, prevents the proximal end of the light guide connector 94a from being heated to a high temperature, and prevents deterioration of the adhesive bonding the light guide bundle 94 and light guide connector 94a. The heat H absorbed by the light guide connector 94a is transmitted to the first cylindrical member 204, and diffused at the same time.

Particularly, in the first, second and fourth examples, the proximal end face of the light guide bundle 94 has only the illumination light incident part γ where the proximal end face of the light guide bundle 94 contacts the inside of the light-emitting surface of the light source 112. Therefore, the light incident on the proximal end face (the light-receiving surface) of the light guide bundle 94 can be efficiently transmitted.

Further, in the first to third examples, the proximal end face of the light guide bundle 94 is circular, and the proximal end face of the light guide connector 94a is annular. This permits use without defining the directions of the peripheries of these parts.

In the example 4, the light source 112 is circular. However, a rectangular form is also possible, as in the first to third examples.

In the embodiments described herein, the LED 118a is used for the light source 112. However, other small light sources such as an organic EL may be used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An illumination apparatus comprising:
   a light source which generates heat when emitting an illumination light from a light-emitting surface;
   a light transmission member which has a light-receiving surface opposed to the light-emitting surface of the light source, to receive the illumination light emitted from the light-emitting surface of the light source, and guides the illumination light from the light source received on the light-receiving surface; and
   a heat radiation member which has an end face arranged along the light transmission member and opposed to the light-emitting surface of the light source, and a contact part in which at least a part of the end face directly contacts the light-emitting surface, which transmits the light generated in the light source, wherein the end face of the heat radiation member has a non-contact part located outside the light-emitting surface of the light source, in addition to the contact part, and wherein the contact part and the non-contact part of the heat radiation member are on the same level.

2. The illumination apparatus according to claim 1, wherein the light-receiving surface of the light transmission member has an illumination light incident part which is at least partially located inside the light-emitting surface of the light source.

3. The illumination apparatus according to claim 1, wherein
   an area of the light-receiving surface of the light transmission member is smaller than an area of the light-emitting surface of the light source, and
   the light-receiving surface of the light transmission member has an illumination light incident part configured to be housed inside the light-emitting surface of the light source.

4. The illumination apparatus according to claim 3, wherein
   the light-emitting surface of the light source is substantially rectangular, and
   the light-receiving surface of the light transmission member is substantially circular and configured to be housed inside the substantially rectangular light-emitting surface.

5. The illumination apparatus according to claim 4, wherein the non-contact part is located outside the light-emitting surface, with respect to each side of the rectangular light-emitting surface of the light source.

6. The illumination apparatus according to claim 1, wherein the light-receiving surface of the light transmission member has an illumination light incident part which is at least partially located inside the light-emitting surface of the light source.

7. The illumination apparatus according to claim 1, wherein the light source is mounted on a mounting substrate which is electrically connected to the opposite side of the light-emitting surface, and has thermal conductivity.

8. The illumination apparatus according to claim 7, wherein the outside surface of the light source is covered with a resin material to form a heat transmission path between the mounting substrate and heat radiation member.

9. The illumination apparatus according to claim 1, wherein the heat radiation member has a cylindrical connector, into which the light transmission member is inserted.

10. The illumination apparatus according to claim 1, wherein
    the light transmission member is a light guide bundle, and
    the light source includes an LED and fluorescent substance covering the LED, configured to emit white light.

11. An endoscope comprising:
    an insertion portion configured to be inserted toward a subject;
    an operation portion which is connected to a proximal end of the insertion portion; and
    an illumination apparatus according to claim 1, in which the light-emitting surface of the light source and the end face of the heat radiation member are directly connected inside the operation portion.

12. The endoscope according to claim 11, wherein the heat radiation member and light source are connected inside the operation portion by a connection member having thermal conductivity.

13. The endoscope according to claim 12, wherein the connection member is provided closely contacting the heat radiation member.

14. The endoscope according to claim 13, wherein
    the light source is mounted on a mounting substrate which is electrically connected to the opposite side of the light-emitting surface, and has thermal conductivity, and
    the connection member is provided with a holding part which is configured to transmit the heat transmitted from the light source to the mounting substrate, and hold the mounting substrate.

15. The endoscope according to claim 12, wherein
    the light source is mounted on a mounting substrate which is electrically connected to the opposite side of the light-emitting surface, and has thermal conductivity, and the connection member is provided with a holding part which is configured to transmit the heat transmitted from the light source to the mounting substrate, and hold the mounting substrate.

16. The illumination apparatus according to claim 1, wherein the end face of the heat radiation member has an annular shape, and the contact part and the non-contact part of the heat radiation member are formed of a part of the annular shape of the end face of the heat radiation member.

17. The illumination apparatus according to claim 1, wherein the end face of the heat radiation member has an annular shape by the contact part and the non-contact part.

* * * * *

UNITED STATES PATENT AND TRADEMARK OFFICE
CERTIFICATE OF CORRECTION

PATENT NO. : 7,959,339 B2  
APPLICATION NO. : 12/210272  
DATED : June 14, 2011  
INVENTOR(S) : Katsushi Watanabe It is certified that error appears in the above-identified patent and that said Letters Patent is hereby corrected as shown below:

In the specification

Column 1, line 44: "light generated" should read -- heat generated --.

In the claims

Column 19, line 46: "light generated" should read -- heat generated --.

Signed and Sealed this  
Third Day of May, 2016

Michelle K. Lee  
*Director of the United States Patent and Trademark Office*